United States Patent [19]
Sonderegger

[11] Patent Number: 5,903,966
[45] Date of Patent: May 18, 1999

[54] METHOD AND APPARATUS FOR NEEDLE-SUTURE ATTACHMENT

[75] Inventor: Marcel Sonderegger, Schaffhaus, Switzerland

[73] Assignee: United States Surgical Corporation, Norwalk, Conn.

[21] Appl. No.: 08/891,144

[22] Filed: Jul. 10, 1997

Related U.S. Application Data

[62] Division of application No. 08/639,704, Apr. 29, 1996, Pat. No. 5,701,664, which is a continuation of application No. 08/297,202, Aug. 29, 1994, abandoned.

[51] Int. Cl.⁶ ...................................................... B23P 19/04
[52] U.S. Cl. ................................ 29/464; 29/468; 29/515; 29/517
[58] Field of Search .............................. 29/241, 433, 464, 29/468, 515, 516, 517, 700, 819, 822; 72/416

[56] References Cited

U.S. PATENT DOCUMENTS

2,411,079  11/1946  Baule .
2,620,028   3/1952  Kohut .
4,054,144  10/1977  Hoffman et al. .
4,060,885  12/1977  Hoffman et al. .
4,229,963  10/1980  Savinov et al. .
4,722,384   2/1988  Matsutani .
4,799,311   1/1989  Matsutani .
4,922,904   5/1990  Uetake et al. .
5,046,350   9/1991  Proto et al. .
5,099,676   3/1992  Proto et al. .
5,230,352   7/1993  Putnam et al. .
5,350,373   9/1994  Colligan .

Primary Examiner—Joseph M. Gorski

[57] ABSTRACT

An apparatus for microsurgical needle suture attachment includes a clamp for holding a needle such that the needle aperture remains in a fixed position; at least one guide member defining an angled guide area having a relatively wide portion and a vertex portion, the vertex portion being aligned with the fixed position of the needle aperture; a transport mechanism for advancing a suture end portion into the relatively wide portion of the guide member(s); and a deflection spring for moving the suture end portion into the vertex portion of the angled guide area.

8 Claims, 9 Drawing Sheets

METHOD AND APPARATUS FOR NEEDLE-SUTURE ATTACHMENT

This is a divisional of U.S. application Ser. No. 08/639,704, filed Apr. 29, 1996, and now U.S. Pat. No. 5,701,664 which is a continuation of U.S. application Ser. No. 08/297,202 filed Aug. 29, 1994 and now abandoned.

BACKGROUND

1. Technical Field

The present method and apparatus relate to the attachment of a suture to a surgical needle.

2. Background of the Art

Surgical needles are well known in the art. A needle used in surgery is from 0.0025 to about 0.06 inches in diameter. Surgical needles are often curved. They typically have a butt, or "barrel" end with an axial hole drilled therein into which a suture is inserted for attachment after the suture is inserted. The needle is crimped or swaged to hold the suture in place. The swaging is performed so as to retain the suture in the needle such that a predetermined pull out force is required to separate the suture from the needle. Pull out forces are standardized and a list of standard pull out forces and suture diameters for a range of standard USP suture sizes is set forth in the U.S. Pharmacopeia. The sutures can be monofilament or multifilament. They can be bioabsorbable or non-bioabsorbable.

Generally, multifilament sutures are tipped prior to needle suture attachment. Multifilament sutures have a tendency to "broom" when cut. The tipping process adheres the filaments and facilitates insertion of the suture end into the hole in the needle.

Methods for attaching sutures to needles are known in the art and are disclosed and described in U.S. Pat. Nos. 5,046,350, 4,922,904, 4,799,311, 4,722,384, 4,072,041, 4,060,885, 4,054,144, and 3,910,282, for example.

However, significant problems occur when dealing with the attachment of microsurgical needles and sutures. Microsurgical needles are typically from about 0.0025 to about 0.0130 inches in diameter. Microsurgical sutures usually used range from about 0.0015 to about 0.0080 inches in diameter. Microsurgical needle-suture attachment procedures are typically assisted by the use of magnification optics such as magnifying lenses or video monitors connected to telescopic magnification optics. As can be expected it is difficult to manipulate sutures which can hardly be seen without magnification. To insert such sutures manually into the hole in the barrel end of a needle, even with magnification, is very time consuming. Yet, surprisingly, this is the method currently being employed. The apparatus now used includes a needle holder which is movable along a track to position the needle between the jaws of a swaging die. Video cameras with telescopic magnification lenses enable the operator to view the end of the needle. The operator holds the suture end between the fingers and slowly advances the suture end, trying to get it aligned with the needle end. It can take a skilled worker up to a minute to insert the suture into the needle and to secure it by swaging.

Clearly, it would be desirable to simplify and speed up the process of microsurgical needle-suture attachment. Accordingly, the apparatus and method described herein reduce the per needle insertion time to as little as 20 seconds. This corresponds to a 200% increase in efficiency with respect to the use of time.

SUMMARY

An apparatus for surgical needle-suture attachment is provided herein. One embodiment of the apparatus is also highly advantageous for the attachment of microsurgical needles and sutures. Another embodiment is advantageous for larger size needles and sutures. The apparatus includes: a frame; a needle positioner for holding a surgical needle such that the needle aperture is in a fixed position; at least one guide member defining an angled guide area having a relatively wide portion and a vertex portion, the vertex portion being aligned with the fixed position of the needle aperture; a transport mechanism mounted to the frame for advancing a suture end portion into said relatively wide portion of the at least one guide member; and a deflection mechanism for moving the suture end portion into said vertex portion of the angled guide area.

The apparatus can further include: a mounting system and first and second dies mounted therein, the first and second dies having mutually opposing edges, the first die being fixedly mounted relative to the mounting system and wherein the needle positioner includes a notch in the first die for receiving a needle, the notch being aligned with the vertex portion of the guide member, and the second die being movable between a first position wherein the first and second dies are spaced apart to define a gap therebetween, and a second position wherein the mutually opposing edges of the first and second dies are in close proximity. Optionally, the needle positioner can include a clamp for holding the needle, the clamp being slidably and removably mounted to the frame.

The transport mechanism includes a conical spacer element, a conical feeder element, and a suture drive mechanism therebetween wherein the suture drive mechanism can include a spindle and roller, the spindle being rotatable in response to manual or powered rotation of an actuator. Alternatively, the suture drive mechanism can also include a pneumatic system having a gas jet nozzle to produce a Venturi effect.

The deflection mechanism can include a resilient lightweight strand which moves the suture end portion laterally into the vertex portion of the angled guide area. The resilient strand is optionally fixedly attached to the second die and has a portion extending beyond the opposing edge of the second die. Alternatively, the deflection mechanism can be a curved surface in the conical spacer element which directs the suture into the insertion guide.

In one embodiment the guide member includes a pair of wires configured into an X-shape. In another embodiment the guide member is a wire configured into an M-shape. In yet another embodiment the guide member includes at least one flat plate having an edge defining a V-shaped angled guide area. Preferably, the apparatus includes two or more guide members with aligned vertices. In yet another embodiment the insertion guide is an elongated member oriented longitudinally and having a V-shaped groove extending longitudinally thereon.

Also described is a method of surgical needle-suture attachment using the apparatus described herein.

DETAILED DESCRIPTION OF PREFERRED EMBODIMENT(S)

The apparatus 100 described herein has three basic portions: a suture advancing portion 100a, a needle mounting portion 100c which positions the needle to receive the suture, and, therebetween, a needle-suture insertion and attachment portion 100b which guides the suture end into the barrel end of the needle, and optionally swages the needle to secure the suture after it has been inserted. The present apparatus preferably is used in conjunction with magnification optics and may employ fiber optic lighting. Such optics are commercially available.

Figure 1:
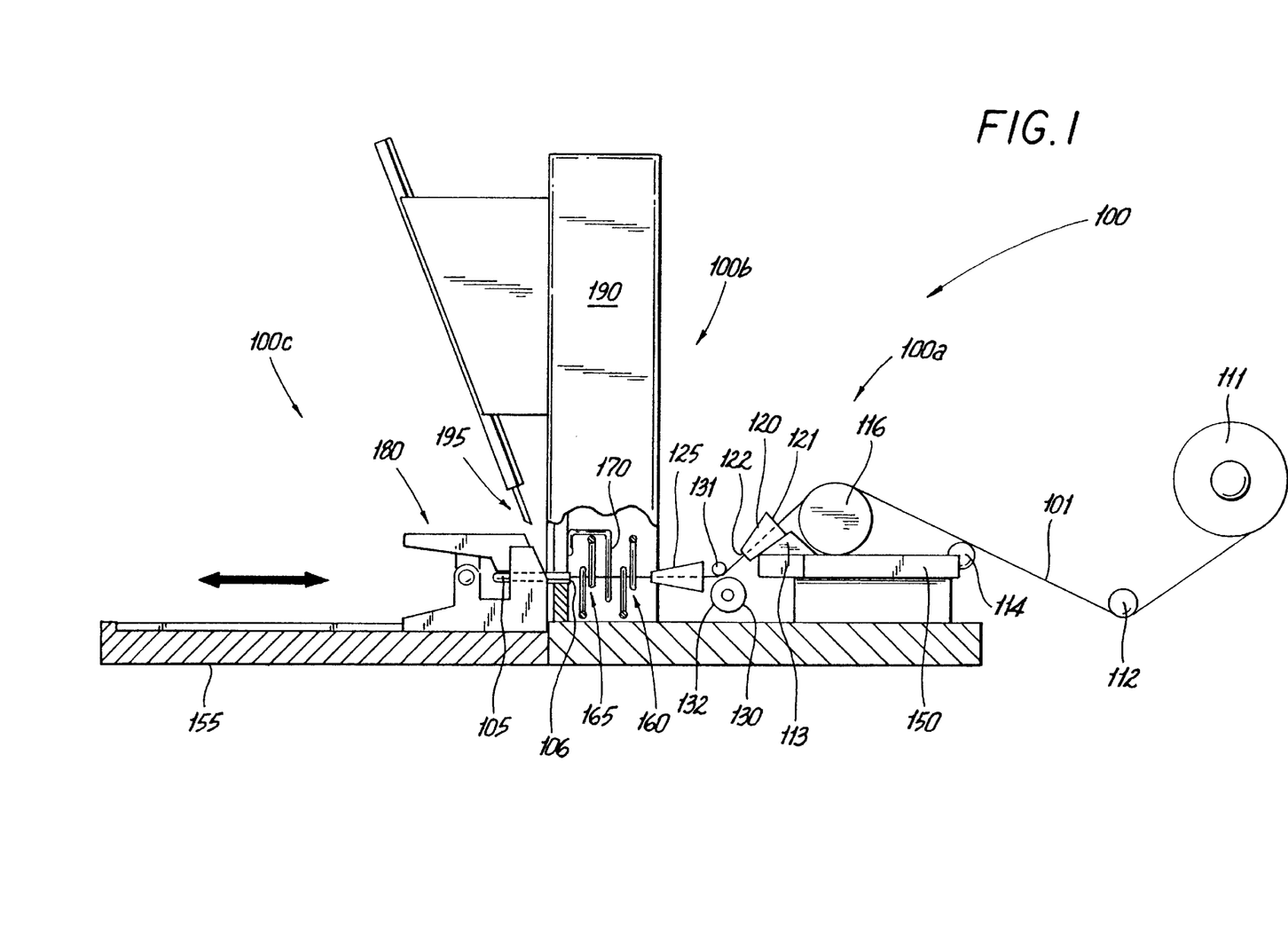
FIG. 1 is a diagrammatic view of the apparatus.

Referring to FIG. 1, a method and apparatus 100 is illustrated wherein a suture 101 is inserted into the barrel end of needle 105. While apparatus 100 may be used for any size suture and needle conventionally used in surgery, it is especially advantageous for microsurgical needle-suture attachment. The microsurgical suture typically ranges in size from diameter from about 1.5 mils to about 8 mils, a "mil" being 0.001 inches. The mlcrosurgical needle is typically about a half inch long and from about 3 mils to about 13 mils in diameter. Such a needle will typically have a suture-receiving aperture 107 in the barrel end portion 106 with the hole having a diameter of from about 2 mils to about 10 mils, which is only slightly larger than the diameter of the suture to be inserted therein. The suture is mostly a monofilament suture and may be fabricated from bioabsorbable material or non-bioabsorbable material. Suitable bioabsorbable materials include polymers of glycolide, lactide, caprolactone, polydioxanone, trimethylene carbonate, and, and mixtures and copolymers thereof, as well as natural collagenous materials. Suitable non-bioabsorbable materials include nylon, polypropylene, polyesters, silk and other such materials.

Figure 2:
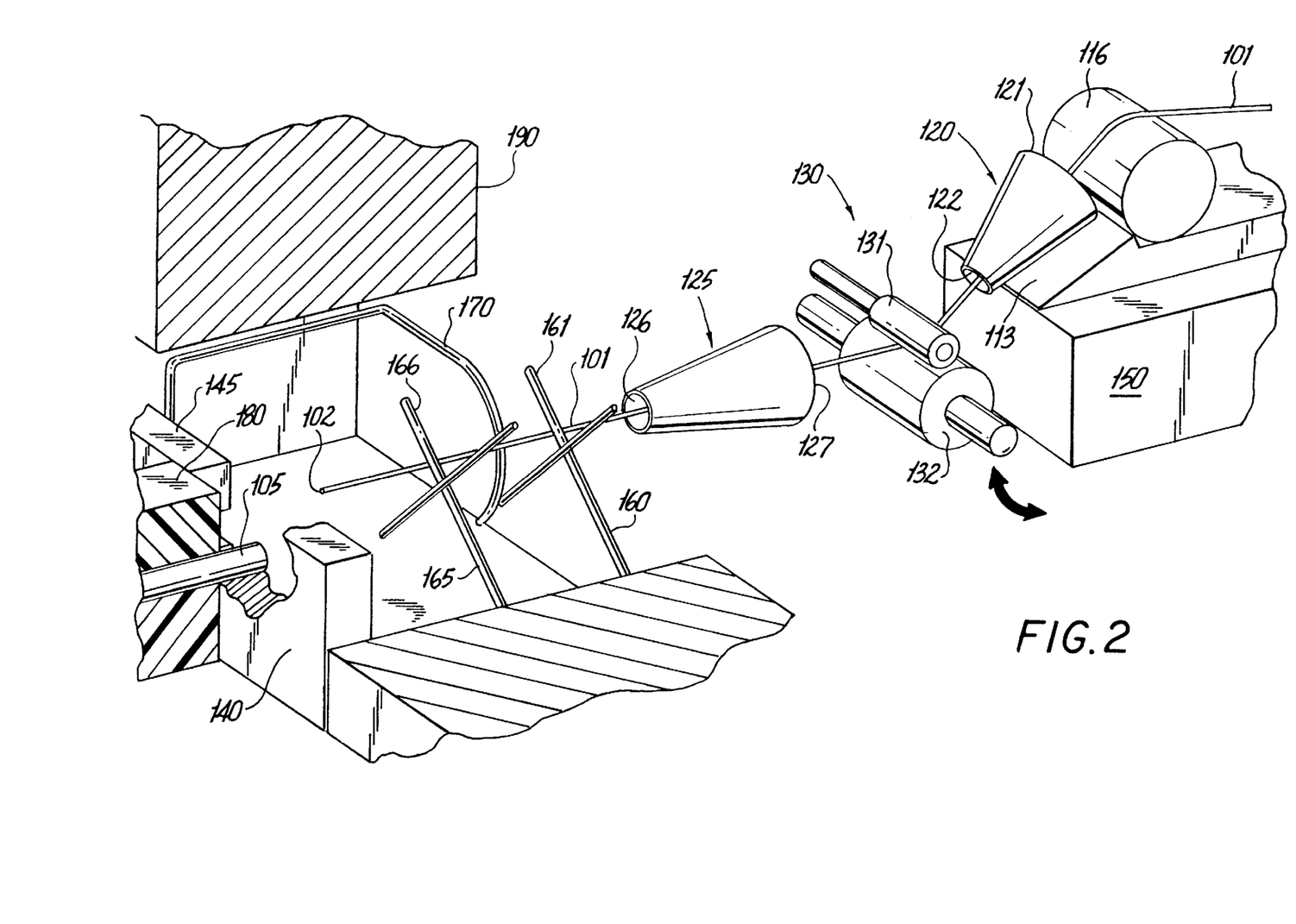
FIG. 2 is a detailed perspective view of a section of the apparatus showing the advancement of a suture end through the insertion guides.

Referring to the suture advancing portion 100a, the suture 101 is initially wound on spool 111 from which it is drawn off. Tension is applied to the suture by means of a tensioning roller 112, or a resilient spring tensioner, to prevent slackness in the suture. The suture 101 is then passed over roller 114 which is rotatably mounted at one end of the work platform 150. Referring additionally to FIG. 2, the suture 101 is optimally then passed over a cylindrical guide member 116 which positions the suture for entry into feeder funnel 120. Guide member 116 can be rotatable or, alternatively, non rotatable; but generally is less than an inch in diameter and preferably has a smooth surface to prevent damage to the delicate suture 101 as the suture passes thereover. It may optionally be fabricated from metal or synthetic polymer. A synthetic polymer suitable for use as a guide cylinder is Dupont self-lubricating DELRIN® AF synthetic resin, which is an acetal resin containing polycetrafluoroethylene. Also useful are polished stainless steel, glass, and smooth ceramics. The cylindrical guide 116 prevents the suture 101 from contacting the edge of the feeder funnel 120.

The apparatus includes a suture transport mechanism for advancing the suture. The transport mechanism includes a conical feeder funnel which can be equipped with a Venturi vacuum generator to draw the suture down through the conical funnel (as explained below), a suture drive, and a conical spacer. Referring to FIGS. 1 and 2, conical feeder funnel 120 is mounted to ramp 113 which positions the funnel 120 at a suitable angle to guide the suture to the suture drive. By way of example, the funnel may be disposed horizontally or up to an angle of about 60 degrees from horizontal. The suture 101 enters funnel 120 at the wide diameter open end 121 and exits at the small diameter open end 122. For attaching sutures to micro-needles having a diameter of less than about 13 mils the wide diameter opening 121 preferably has a diameter of about 0.2 inches and the small diameter exit opening 122 preferably has a diameter of about 0.04 inches. Suture 101 is then passed through suture drive 130, which preferably includes rotating spindle 131 and freely rotatable roller idle 132, the suture 101 being passed therebetween. Roller 132 is laterally movable in a direction toward or away from spindle 131 in response to a mechanical or electrically operated switch (not shown) actuated by the operator to permit release of the suture 101. Advance of the suture is controlled by a manually operated hand crank (not shown) which turns spindle 131. The switch and hand crank mechanisms are known and commercially available. It is also contemplated that the spindle 131 and/or roller idle 132 may be motor driven. The suture 101 thereafter enters a spacer cone 125 which guides the suture 101 to the suture insertion guides 160 and 165. For micro-needle suture attachment the spacer cone 125 preferably has an entrance opening 127 with a diameter of about 0.2 inches and an exit opening 126 with a diameter of about 0.04 inches.

Figure 11:
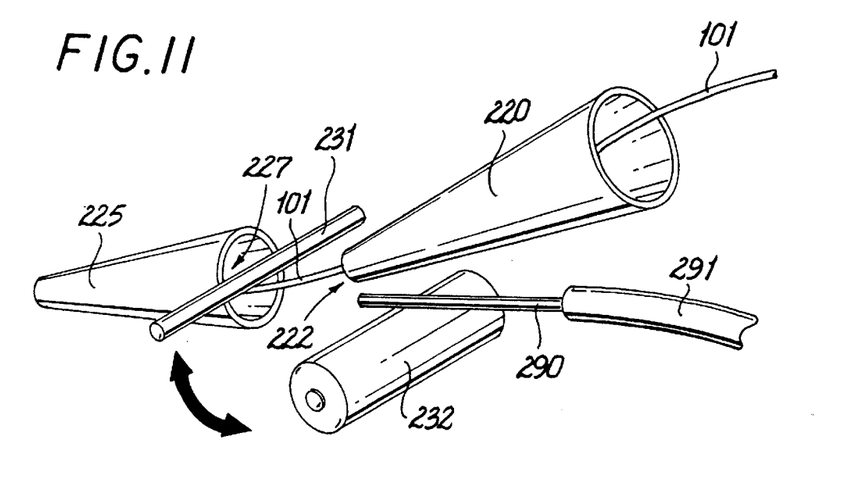
FIG. 11 is a diagrammatic perspective view of an embodiment using a pneumatic feeding assist.

In an alternative embodiment a pneumatic feeding mechanism facilitates the insertion of the sutures into the conical spacer using a jet of air or other gas. Referring to FIG. 11, a suture 101 is passed into a conical feeder funnel 220. A jet nozzle 290 is positioned in proximity to the small diameter outlet end 222 of the feeder funnel 220 and is oriented so as to blow a jet of gas across the outlet end 222 and into the large diameter inlet end 227 of the conical spacer 225. The gas jet generates a venturi effect with a concomitant low pressure area, or partial vacuum, in the vicinity of the outlet 222, thereby drawing the suture out of the conical feeder and directing it into the conical spacer 225. The jet nozzle 290 is coupled to a flexible tube 291 which carries compressed air or other gas from a supply (not shown). The spindle 231 and roller idle 232 are initially spaced apart to permit the gas jet to blow the suture therebetween. After the suture 101 is inserted into the conical spacer 225 the roller idle 232 may be moved up into contact with the spindle 231 to hold the suture 101 therebetween for transport.

Figure 5:
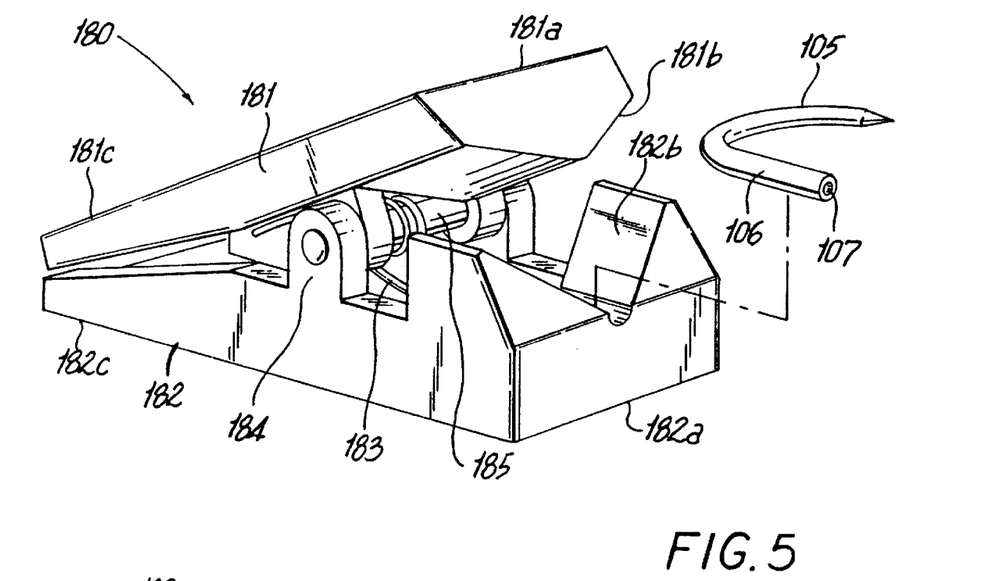
FIGS. 5 and 6 are perspective views showing the needle clamp in the open and closed positions, respectively.
Figure 6:
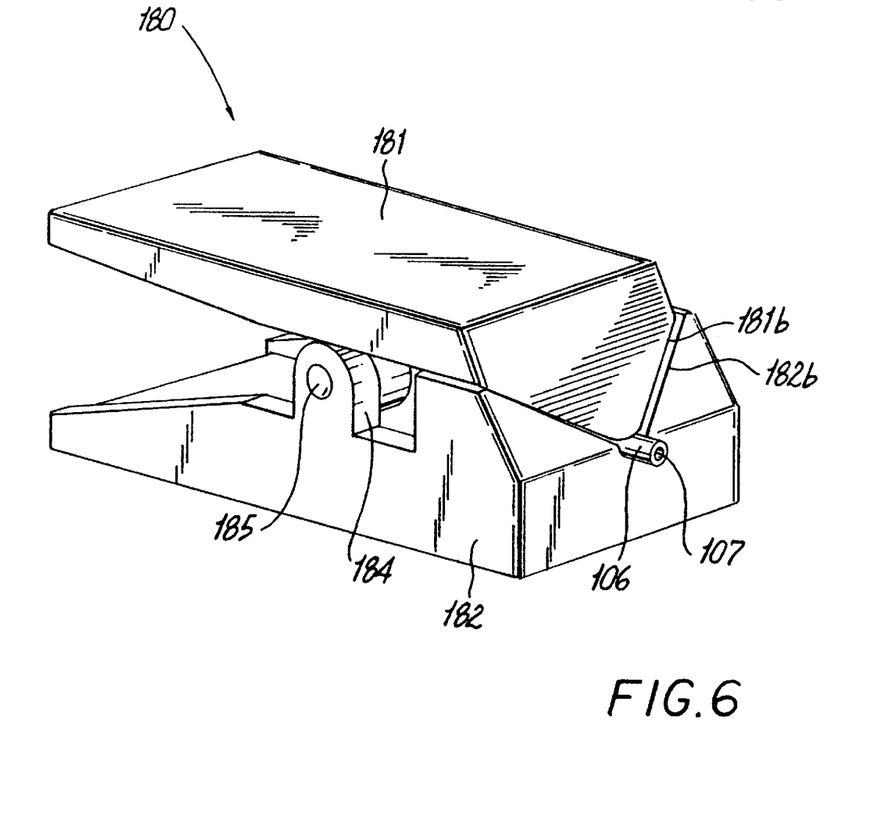

Referring now to FIGS. 5 and 6, the needle 105 is mounted in a clamp or needle holder 180 such that the barrel end portion 106 of the needle extends beyond the needle holder 180. Needle holder 180 includes two hingedly connected members, upper member 181 and lower member 182. Hinge portion 184 includes shaft 185 extending laterally across. Spring 183 biases the members to a closed position. Upper member 181 includes a forward needle mounting portion 181a having an projection 181b with an angled needle contacting surface, and a rear portion 181c on the outer side of the hinge portion 184. Lower member 182 includes a needle mounting portion 182a having a V-shaped needle reception groove 182b for receiving projection 181b and a rear portion 182c. When the rear portion 181c and 182c are pressed together, the needle mounting portions 181a and 182a open up for placement of a needle therebetween. After the needle is placed, the rear portions 181c and 182c are released to allow the spring 183 to bias the needle mounting portions 181a and 182a to a closed position.

Figure 7:
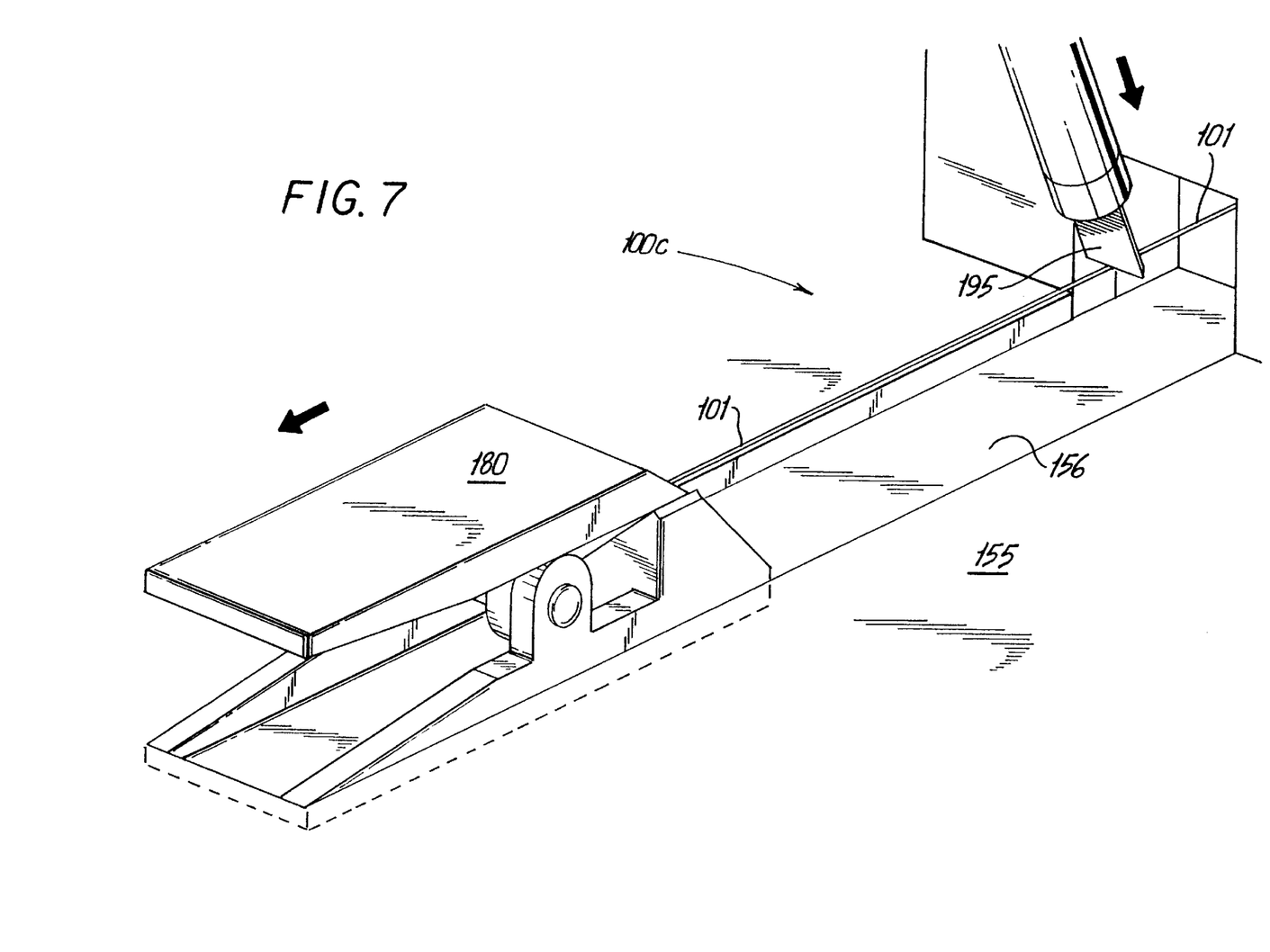
FIG. 7 is a perspective view showing positioning of the needle clamp in a track.

Referring to FIGS. 1 and 7, the needle positioning portion 100c of the apparatus 100 includes a platform 155 with a longitudinal oriented track 156, wherein "longitudinally" means along the processing line along which the suture 101 travels lengthwise. The length of the groove 156 can be used to determines the desired length of the suture strand attached to the needle 105 after cutting. The needle holder 180 with needle 105 is positioned such that the barrel end portion 106 of the needle is in contact with the stationary first die 140 of the suture attachment section.

Referring to FIGS. 1, 2, 2A, 3 and 4, the needle suture attachment portion 100b of the apparatus includes a housing 190 having a rotatable mounting system for swaging dies. A rotatable mounting system useful in the present apparatus is disclosed in U.S. patent application Ser. No. 07/959,114 filed Oct. 9, 1992, and herein incorporated by reference.

In the present apparatus, a first die 140 is stationary with respect to the rotatable mounting system and includes a crimping surface 141 having a needle-receiving hemicylindrical notch 142 dimensioned to receive the barrel end portion 106 of the needle. The hemicylindrical notch 142 is the center of rotation of the rotatable mounting system such that dies 140 and 145 can be rotated around a stationary needle. The opposing second die 145 is movable and includes a crimping surface 146 having a corresponding notch 147 adapted to contact the side of the needle opposite the first die 140. When the two crimping surfaces 141 and 146 are brought together they cause the wall of the needle 105 to collapse inwardly to grip the suture 101 inserted therein. Any suitable crimping die configuration may be used, including lap-overlap or staking dies. Other dies are disclosed in U.S. Pat. Nos. 5,046,350 and 5,099,676.

Figure 2A:
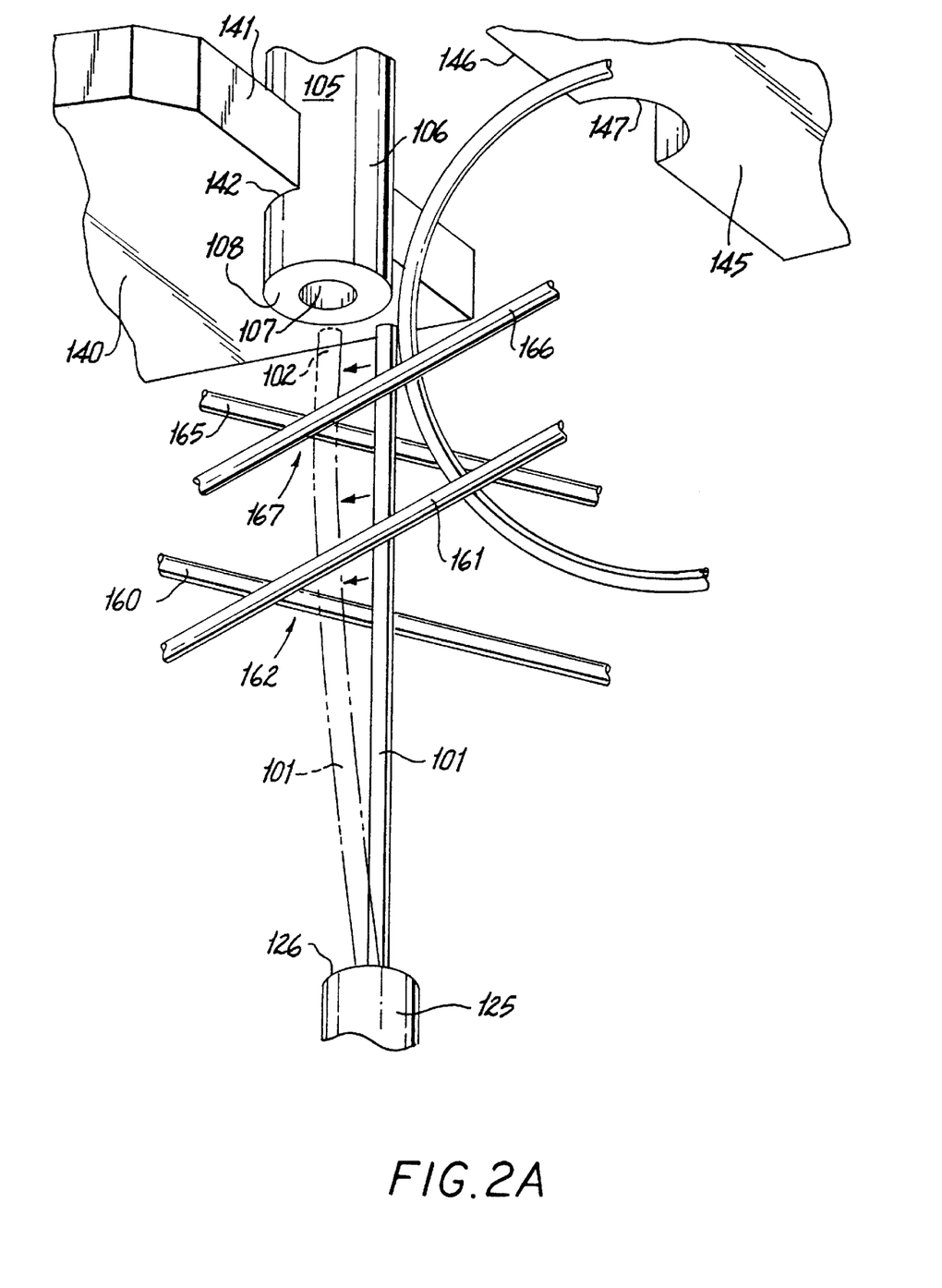
FIG. 2A is a perspective view showing suture deflection in the guides to a position aligned with the needle hole.
Figure 3:
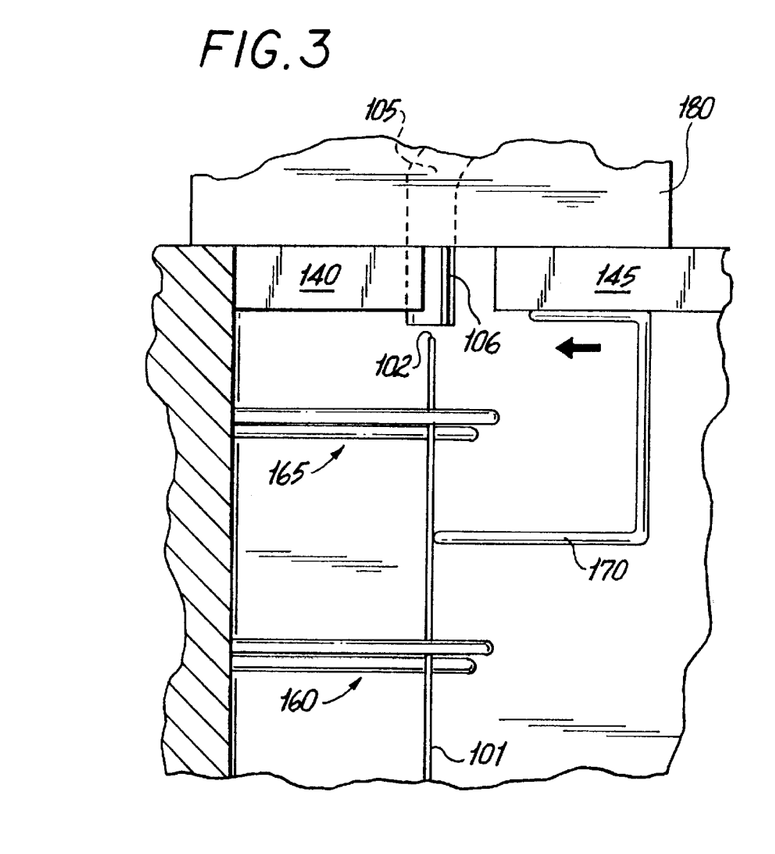
FIG. 3 is a plan view showing the suture aligned with the needle.

The needle-suture attachment portion 100b also includes at least one, and preferably two or more insertion guides 160 and 165 for guiding the suture into proper position for insertion into the hole 107 in the barrel end portion 106 of the needle. The insertion guides each include a substantially V-shaped portion 161 and 166, respectively, having a vertex area 162 and 167, respectively, into which the suture 101 is moved, as explained below. The angle defined by the V-shaped area can range from between 0° and 180°, but preferably ranges from about 20° to about 100° and more preferably from about 40° to about 80°. The guides 160 and 165 shown in FIGS. 2 and 2A are X-shaped arrangements of guide wires, the vertex areas 162 and 167 being aligned with the hemicylindrical notch 142 of the first die 140. Also useful are M-shaped guide wires illustrated in FIG. 8. For micro-needle attachment the insertion guides 160 and 165 are spaced apart about 15 mils from each other. Insertion guide 165 is preferably about 10 mils away from the surface of the stationary first die 140. The insertion guides are illustrated as presenting a lazy V-shaped guiding area, i.e. the V-shaped guide area is oriented on its side. As explained below, the suture is biased laterally by a spring member into the V-shaped portion of the guide area. However, alternative embodiments wherein the V-shaped portion is upright are also useful. In such an embodiment the spring preferably operates vertically downward.

Guide wires for insertion guide 160 and 165 can have a diameter of a fraction to a multiple of the suture diameter. It is preferable that the guide wires be fabricated from a metal or other electrically conductive material to prevent the build-up of a static electricity charge.

The apparatus includes at least one deflector for moving the suture laterally into the vertex portions 162 and 167 of the angled guide areas. Preferably, the deflector is a resilient spring mechanism. Referring to FIGS. 2, 2A, 3 and 4, the spring 170 preferably includes a resilient wire or filament and is preferably of smaller diameter than the suture. The deflector spring is preferably fixedly attached to the movable second die 145 and extends beyond the crimping surface 146 of the second die. Spring 170 is positioned to move between or in front of the insertion guides 160 and 165. For increased accuracy, insertion guides may be employed with multiple springs, each spring being positioned to move between or in front of the insertion guides. The spring 170 is weakly resilient, its force being just sufficient to move the suture 101 without bending it or causing damage thereto. Optionally the first spring after the conical spacer can be stiffer than the others in order to provide stronger initial deflection for forcing the suture into the insertion guides. When the suture 101 is inserted into the hole 107 in the needle and resists further lateral movement, spring 170 easily gives way by bending. By way of example, the spring can be fabricated from a looped strand of monofilament suture material or a thin metal wire.

Referring to FIGS. 2, 2A, 3 and 4, initially, needle 105 is positioned such that the barrel end portion 106 is engaged in notch 142. The end surface 108 of the needle can extend a short distance beyond the die 140 in order to space the intended crimp in the needle away from the end surface 108. The second die 145 is spaced apart from the first die 140 leaving a gap therebetween. The suture 101 is initially advanced through spacer cone 125 until the end 102 of the suture passes through both of the insertion guides 160 and 165. As can be seen from FIG. 2A, the exit end 126 of the spacer cone is laterally offset from the notch 142 and vertices 162 and 167 of the guide areas. This is a significant feature since it allows variability in the position of the suture end 102 to be encompassed by the V-shaped guide areas 161 and 166, and therefore permits the position of the suture end 102 to be controlled by the operator as he or she moves the suture 101 down into the vertices 162 and 167 of the guides. Alternatively, the spacer cone 125 can be aligned with the notch 142 but angled to position the suture end 102 into the relatively wider portion of the V-shaped guide areas 161 and 166.

Figure 4:
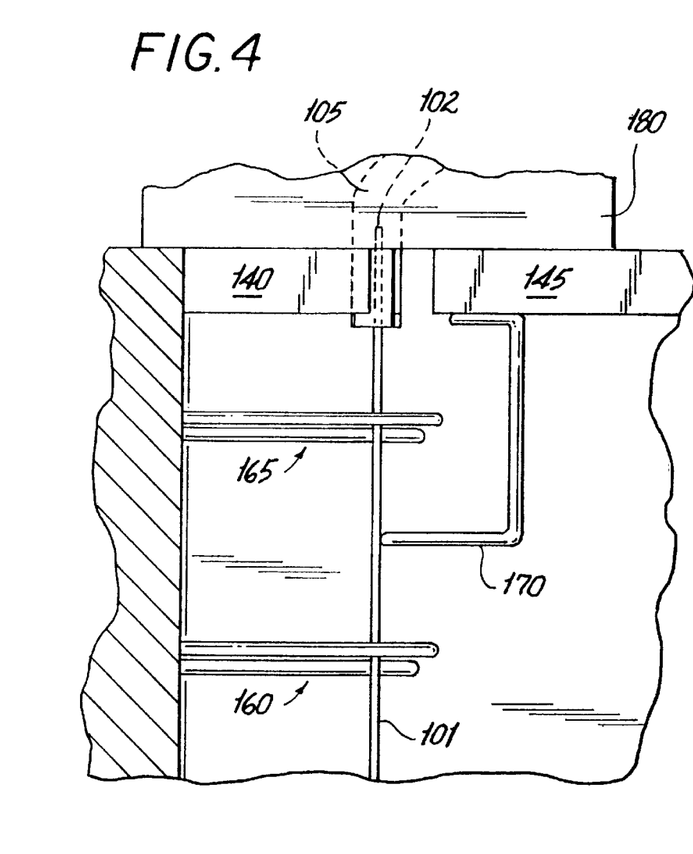
FIG. 4 is a plan view showing insertion of the suture into the needle.

Next, the second die 145 is moved toward the first die 140 and spring 170 biases the suture deeper into the V-shaped portions 161 and 166 of the guide areas until the suture 101 is situated at the vertices 162 and 167 of the V-areas, wherein the suture 101 is in alignment with the hole 107 of the needle, as shown in FIGS. 2A and 4. Next the suture 101 is advanced into the hole 107. Then the second die 145 is moved further to contact the needle 105, thereby swaging it and securing the suture 101 therein. The dies may be opened, rotated, and closed again for double hit or further multiple hit swaging.

Finally, as shown in FIG. 7, the needle holder 180 is moved back along track 156 to draw a predetermined length of suture 101. A cutting blade such as knife 195 or a scissors is then used to sever the suture 101 with an angled cut. The cutting mechanism can also be located between the insertion guides 260, 265 and the conical spacer 125.

Figure 8:
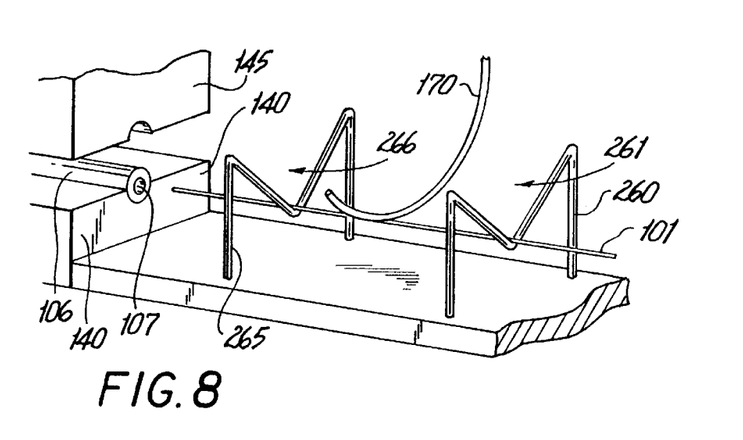
FIG. 8 is a perspective view of an alternative M-shaped embodiment of the insertion guide.

Referring to FIG. 8, an alternative embodiment of the insertion guides is shown wherein insertion guides 260 and 265 are M-shaped and have V-shaped guide areas 261 and 166, respectively.

Figure 9:
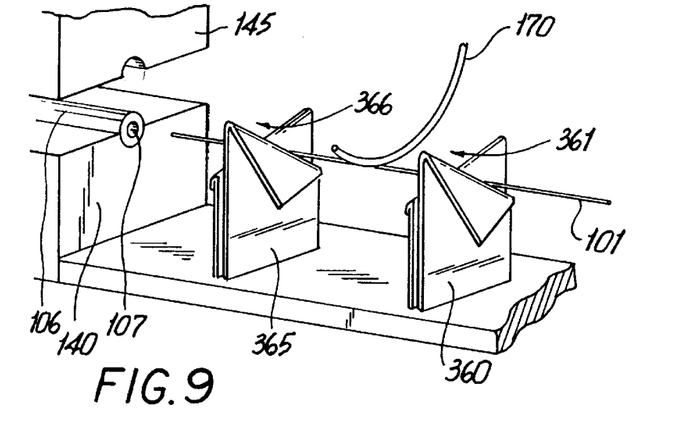
FIG. 9 is a perspective view showing a yet another embodiment of the insertion guide.

Referring to FIG. 9, a further alternative embodiment of the insertion guides is shown wherein the insertion guides 360 and 365 are pairs of plates, each pair having top (as shown) edges forming V-shaped guides areas 361 and 366, respectively. These plates may be fabricated from metal or plastic.

Figure 10A:
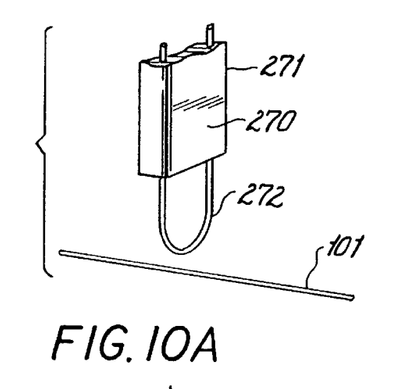
FIGS. 10A and 10B are perspective views showing a gravity operated embodiment of the deflection spring.
Figure 10B:
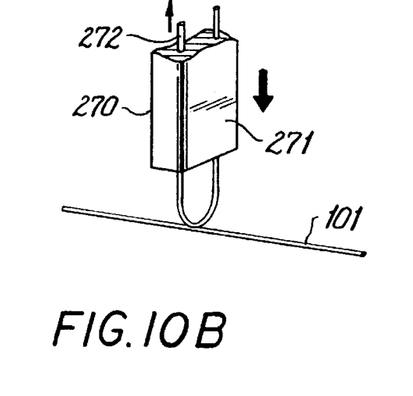

Referring to FIGS. 10A and 10B, an alternative embodiment of the deflector is shown wherein deflector 270 includes a mounting support 271 and a spring wire or filament 272 which is slidably and loosely mounted to the mounting support 271. Deflector 270 operates vertically. Wire 272 drops naturally under the influence of gravity, or artificially by the influence of a spring or air, to a lower position with respect to the mounting support 271. Wire 272 is prevented from dropping out of the mounting support 271 by a suitable stop surface (not shown). When spring 270 is moved downward to bias the suture 101, the wire 272 easily slides upward with respect to the mounting support 271 when it encounters resistance by the suture 101, as for example, when the suture has been inserted into the hole in the needle. The weight of wire 272 must be suitable to accomplish the function described herein. Too light a wire might not drop reliably; too heavy a wire might not retract reliably. The proper weight is easily determined by one with skill in the art. Wire 272 can be fabricated from metal or nonmetal such as synthetic polymer. Suture material can be used to fabricate wire 272.

Figure 12:
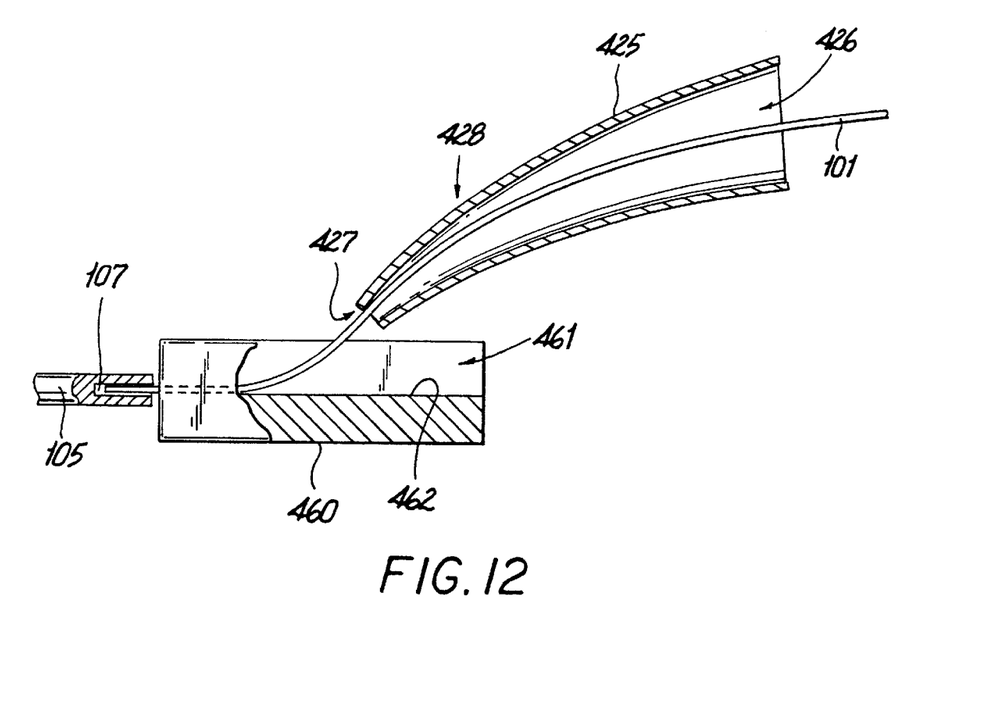
FIGS. 12 and 13 are, respectively, a partly sectional side view and a perspective view of an alternative embodiment of the apparatus employing a curved conical spacer.
Figure 13:
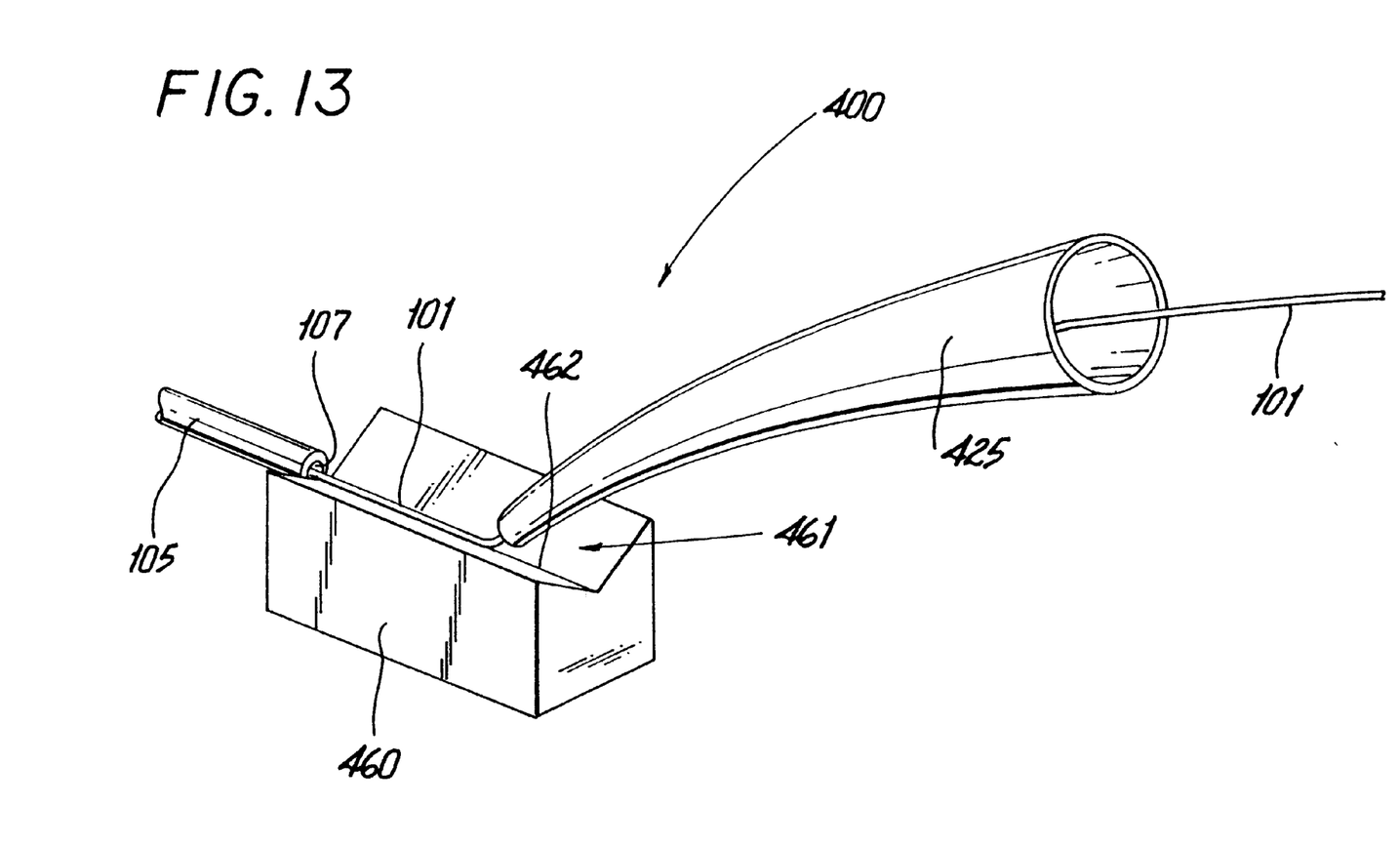

Referring to FIGS. 12 and 13 alternative embodiments of the conical spacer 425 and insertion guide 460 are shown which are advantageous for use with sutures of USP sizes 8–0 and larger, i.e. diameters of over about 0.040 mm. Such sutures possess sufficient stiffness such that the frictional forces encountered by the suture upon contacting the walls of the conical feeder or conical spacer do not significantly inhibit passage of the suture therethrough. FIGS. 12 and 13 show only the conical spacer, the insertion guide, and the needle, the rest of the apparatus being substantially the same as depicted in FIG. 1. In this embodiment the conical spacer 425 is curved such that a suture 101 entering the spacer 425 through the large diameter inlet 426 impinges the inside surface of the spacer wall at the curved portion 428 and is deflected downward, sliding along the upper inner surface of the spacer 425. The insertion guide 460 is an elongated longitudinally oriented member having a V-shaped groove 461 extending longitudinally thereon. The V-shaped groove 461 has a vertex portion 462 for guiding the suture. Outlet opening 427 is positioned over the insertion guide 460 such that the suture 101 enters the V-shaped portion 461 of the insertion guide and is biased downward into the vertex portion 462 of the insertion guide. The vertex portion 462 is aligned with the aperture 107 of needle 105. As the suture 101 is slid forward in insertion guide 460 it enters the needle aperture 107. The needle 105 may be hand held, but is preferably mounted in accordance with the system 100c described above.

It will be understood that various modifications may be made to the embodiments disclosed herein. The above description should not be construed as limiting, but merely as exemplifications of preferred embodiments. Those skilled in the art will envision other modifications within the scope and spirit of the claims appended hereto.

As used in the claims, the term "drive means" is intended to refer to the rollers (131, 132) and/or the Venturi system (290). The term "transport means" is intended to refer to the conical spacer element (125,425) and the conical feeder (120) in combination with the drive means.

As used in the claims, the term "deflection means" is intended to refer to a spring wire or filament (170), or a bent surface (428) of the conical spacer (425).

What is claimed is:

1. A method for attaching a suture to a surgical needle comprising:

a) providing a suture with a diameter of less than about 10 mils and having an end portion for insertion into an aperture in a surgical needle;

b) providing a needle with an aperture having a diameter dimensioned to receive said suture end portion and hold said suture when said needle is swaged;

c) holding said needle such that the suture receiving aperture is in a fixed position;

d) providing at least one guide member defining an angled guide area having a relatively wide portion and a vertex portion, said vertex portion being aligned with the fixed position of the needle aperture;

e) providing a deflection means for contacting and laterally deflecting said suture end portion, said deflection means being movable in a direction transverse to the linear orientation of the suture;

f) moving said suture end portion into said relatively wide portion of the guide area; then g) moving the deflection means into contact with said suture end portion to apply a lateral deflection force thereto, said suture end portion being moved into the vertex portion of the guide area in response to application of the lateral deflection force; then h) moving said suture end portion into said aperture in said needle; and, i) deforming a portion of the needle such that the suture becomes affixed within said aperture.

2. The method of claim 1, wherein said deforming step includes swaging the portion of the needle, and further including the step of cutting said suture.

3. The method of claim 1 wherein the angled guide area of the at least one guide member is a V-shaped angled guide area formed by a pair of wires configured into an X-shape.

4. The method of claim 1 wherein the angled guide area of the at least one guide member is a V-shaped angled guide area formed by a wire configured into an M-shape.

5. The method of claim 1 wherein the angled guide area of the at least one guide member is a V-shaped angled guide area formed from at least one flat plate presenting at least one edge defining the V-shaped angled guide area.

6. The method of claim 1 wherein the angled guide area is disposed in a plane transverse to an axis of the surgical needle aperture.

7. The method of claim 6 wherein the deflection means is movable in a direction substantially parallel to the plane of the guide area.

8. The method of claim 1 wherein the step of moving the suture end portion into the relatively wide portion of the guide area includes:

a) passing the suture end portion through a conical feeder;

b) blowing a jet of gas across an outlet of the conical feeder to direct the suture end portion into a conical spacer;

c) passing the suture end portion through the conical spacer;

d) moving a spindle and roller idle into contact with the suture such that relative rolling of the spindle and roller idle effects linear movement of the suture.

\* \* \* \* \*